United States Patent
Monello et al.

(10) Patent No.: US 8,551,458 B2
(45) Date of Patent: Oct. 8, 2013

(54) COMPOSITION CONTAINING A HYDROXYLATED DIPHENYLMETHANE DERIVATIVE

(75) Inventors: Aldo Monello, Savigny sur Orge (FR); Melanie Achram, Paris (FR)

(73) Assignee: L'Oreal, Paris (FR)

( * ) Notice: Subject to any disclaimer, the term of this patent is extended or adjusted under 35 U.S.C. 154(b) by 292 days.

(21) Appl. No.: 12/854,918

(22) Filed: Aug. 12, 2010

(65) Prior Publication Data

US 2011/0052512 A1 Mar. 3, 2011

Related U.S. Application Data

(60) Provisional application No. 61/240,321, filed on Sep. 8, 2009.

(30) Foreign Application Priority Data

Aug. 28, 2009 (FR) ...................... 09 55877

(51) Int. Cl.
| | |
|---|---|
| *A61K 8/00* | (2006.01) |
| *A61K 8/18* | (2006.01) |
| *A61K 8/30* | (2006.01) |
| *A61K 8/34* | (2006.01) |
| *A61K 31/05* | (2006.01) |

(52) U.S. Cl.
USPC ....... 424/62; 424/70.19; 424/70.31; 514/724; 514/730; 514/731; 514/734; 514/738

(58) Field of Classification Search
None
See application file for complete search history.

(56) References Cited

U.S. PATENT DOCUMENTS

| | | | |
|---|---|---|---|
| 2006/0147396 A1* | 7/2006 | Monello | ..................... 424/59 |
| 2007/0269390 A1 | 11/2007 | Inoue | |
| 2009/0130035 A1 | 5/2009 | Lange et al. | |
| 2009/0162305 A1 | 6/2009 | Vielhaber et al. | |

FOREIGN PATENT DOCUMENTS

| | | |
|---|---|---|
| DE | 199 35 763 | 2/2001 |
| EP | 1 847 247 | 10/2007 |
| EP | 1 857 095 | 11/2007 |
| EP | 2 100 585 | 9/2009 |
| WO | WO 02/19984 | 3/2002 |

* cited by examiner

*Primary Examiner* — James H. Alstrum-Acevedo
(74) *Attorney, Agent, or Firm* — Oblon, Spivak, McClelland, Maier & Neustadt, L.L.P.

(57) ABSTRACT

The invention relates to a composition in the form of an oil-in-water emulsion containing an ester of fatty acid and of polyethylene glycol, an additional surfactant chosen from esters of $C_{16}$-$C_{22}$ fatty acid and of sorbitan and esters of $C_{16}$-$C_{22}$ fatty acid and of glycerol, a polycondensate of ethylene oxide and of propylene oxide consisting of polyethylene glycol and polypropylene glycol blocks, and a hydroxylated diphenylmethane derivative. The composition has good stability, in particular after 24 hours at 55° C. Application in caring for and making up keratinous substances.

19 Claims, No Drawings

COMPOSITION CONTAINING A HYDROXYLATED DIPHENYLMETHANE DERIVATIVE

REFERENCE TO PRIOR APPLICATIONS

This application claims priority to U.S. provisional application Ser. No. 61/240,321, filed Sep. 8, 2009; and to French patent application 09 55877, filed Aug. 28, 2009, both incorporated herein by reference.

FIELD OF THE INVENTION

One subject-matter of the present invention is an oil-in-water emulsion comprising a hydroxylated diphenylmethane derivative and a specific surfactant mixture.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. In this regard, the description herein is to be understood as illustrative in nature, and not as restrictive.

BACKGROUND OF THE INVENTION

It is known to use active principles in cosmetic and/or dermatological compositions, for example for the purpose of caring for or treating or contributing beneficial effects to the skin. However, some of these active principles exhibit the disadvantage of being unstable in conventional cosmetic solvents and/or of easily decomposing, in particular on contact with water, especially because of phenomena of oxidation. They thus rapidly lose their activity over time and this instability conflicts with the desired effectiveness.

Hydroxylated diphenylmethane derivatives are known from Application US 2007/098655 in compositions in the emulsion form. These hydroxylated diphenylmethane derivatives are described in this patent application as tyrosinase inhibitors which can be used in particular in depigmenting compositions.

These hydroxylated diphenylmethane derivatives, in particular due to their aromatic structure and their lipophilic nature, exhibit the disadvantage of being unstable and/or sparingly soluble in the conventional solvents used in cosmetics. They can in particular recrystallize. In addition, they can easily decompose by light and/or heat, in particular because of phenomena of oxidation. They thus rapidly lose their activity over time and this instability conflicts with the desired effectiveness.

Moreover, the use hydroxylated diphenylmethane derivatives, such as 4-(1-phenylethyl)-1,3-dihydroxybenzene, in emulsions, in particular in oil-in-water emulsions, especially when they comprise a surfactant system comprising an ester of fatty acid and of polyethylene glycol, and an additional surfactant chosen from esters of $C_{16}$-$C_{22}$ fatty acid and of sorbitan and esters of $C_{16}$-$C_{22}$ fatty acid and of glycerol, has a tendency to destabilize the emulsion, which then exhibits a phase separation of oil at the surface. The oil globules dispersed in the aqueous phase have a coarse appearance, rendering the emulsion nonhomogeneous.

SUMMARY OF THE INVENTION

One aim of the present invention is thus to make available an emulsion comprising a hydroxylated diphenylmethane derivative and the surfactant system described above which is stable, in particular for 24 hours at 55° C., indeed even for 2 months at 45° C.

The inventors have discovered that the stability of such an emulsion can be obtained by adding a polycondensate of ethylene oxide and of propylene oxide.

DETAILED DESCRIPTION OF THE PREFERRED EMBODIMENTS

More specifically, a subject-matter of the invention is a composition in the form of an oil-in-water emulsion comprising:
  a hydroxylated diphenylmethane derivative as described below;
  an ester of fatty acid and of polyethylene glycol;
  an additional surfactant chosen from esters of $C_{16}$-$C_{22}$ fatty acid and of sorbitan and esters of $C_{16}$-$C_{22}$ fatty acid and of glycerol;
  a polycondensate of ethylene oxide and of propylene oxide.

Another subject-matter of the invention is a non-therapeutic method for caring for or making up keratinous substances, comprising the application, to the keratinous substances, of the composition defined above.

The hydroxylated diphenylmethane derivatives which can be used in the compositions of the invention are described in Application WO2004/105736, incorporated herein by reference.

These compounds have the following formula (I):

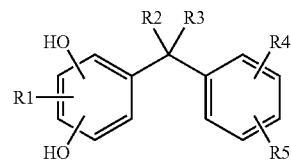

in which:
  R1 is chosen from a hydrogen atom, a methyl group, a saturated or unsaturated and linear or branched alkyl chain having from 2 to 4 carbon atoms, an OH group and a halogen,
  R2 is chosen from a hydrogen atom, a methyl group or a saturated or unsaturated and linear or branched alkyl chain having from 2 to 5 carbon atoms,
  R3 is chosen from a methyl group or a saturated or unsaturated and linear or branched alkyl chain having from 2 to 5 carbon atoms,
  R4 and R5 are chosen, independently of one another, from a hydrogen atom, a methyl group, a saturated or unsaturated and linear or branched alkyl chain having from 2 to 5 carbon atoms, an —OH group or a halogen.

The —OH, R1, R4 and R5 groups can be in the ortho, meta or para positions with respect to the bond formed with the carbon connecting the two aromatic nuclei to one another.

The enantiomeric forms of S configuration, the enantiomers of R configuration and their racemic mixture are also included in the compounds of the invention which have substituted phenyl groups and for which R2 and R3 are different.

According to a preferred form of the invention, use is made of a compound of formula (I) in which:
R1, R2, R4 and R5 denote a hydrogen atom;
R3 is a methyl group;
the —OH groups are in the ortho and para positions with respect to the bond formed with the carbon connecting the two aromatic nuclei to one another.
This compound corresponds to the following formula (II):

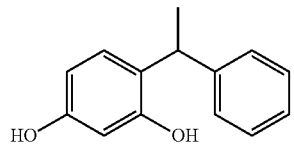 [SMILES: CC(c1ccccc1)c1ccc(O)cc1O]

called 4-(1-phenylethyl)-1,3-benzenediol or 4-(1-phenylethyl)-1,3-dihydroxybenzene or otherwise called phenylethyl resorcinol or phenylethylbenzenediol or styrylresorcinol. This compound has a number CAS 85-27-8.

Such a compound is sold under the name SymWhite 377® or Bio 377 by Symrise.

The hydroxylated diphenylmethane derivative as described above can be present in the emulsion according to the invention in a content ranging for example from 0.01% to 5% by weight, with respect to the total weight of the composition, preferably ranging from 0.01% to 2% by weight and preferentially ranging from 0.01% to 1% by weight.

The composition according to the invention comprises, as main emulsifying surfactant, at least one ester of fatty acid and of polyethylene glycol.

The ester of fatty acid and of polyethylene glycol present in the composition according to the invention is preferably a $C_{16}$-$C_{22}$ fatty acid ester comprising from 8 to 100 ethylene oxide units.

The fatty chain of the esters can be chosen in particular from stearyl, behenyl, arachidyl, palmityl or cetyl units and their mixtures, such as cetearyl, and preferably a stearyl chain.

The number of ethylene oxide units can range from 8 to 100, preferably from 10 to 80 and better still from 10 to 50. According to a specific embodiment of the invention, this number can range from 20 to 40.

Mention may be made, as examples of ester of fatty acid and of polyethylene glycol, of stearic acid esters respectively comprising 20, 30, 40, 50 or 100 ethylene oxide units, such as the products respectively sold under the names Myrj 49 P (polyethylene glycol 20 EO stearate; CTFA name: PEG-20 stearate), Myrj 51, Myrj 52 P (polyethylene glycol 40 EO stearate; CTFA name: PEG-40 stearate), Myrj 53 and Myrj 59 P by Croda.

The ester of fatty acid and of polyethylene glycol can be present in the composition according to the invention in a content ranging for example from 0.1% to 10% by weight, with respect to the total weight of the composition, preferably ranging from 0.1% to 5% by weight and preferentially ranging from 0.1% to 3% by weight.

The composition according to the invention also comprises an additional emulsifying surfactant chosen from esters of $C_{16}$-$C_{22}$ fatty acid and of sorbitan and esters of $C_{16}$-$C_{22}$ fatty acid and of glycerol.

According to a first embodiment of the invention, the composition comprises an ester of $C_{16}$-$C_{22}$ fatty acid and of sorbitan.

The esters of $C_{16}$-$C_{22}$ fatty acid and of sorbitan are formed by esterification, with sorbitol, of at least one fatty acid comprising at least one saturated or unsaturated linear alkyl chain respectively having from 16 to 22 carbon atoms. These esters can be chosen in particular from sorbitan stearates, behenates, arachidates, palmitates or oleates, and their mixtures. Use is preferably made of sorbitan stearates and palmitates and preferentially sorbitan stearates.

The ester of $C_{16}$-$C_{22}$ fatty acid and of sorbitan present in the composition according to the invention is advantageously solid at a temperature of less than or equal to 45° C.

Mention may be made, as examples of sorbitan ester which can be used in the composition according to the invention, of the sorbitan monostearate (CTFA name: Sorbitan stearate) sold by Croda under the name Span 60, the sorbitan tristearate sold by Croda under the name Span 65 V, the sorbitan monopalmitate (CTFA name: Sorbitan palmitate) sold by Croda under the name Span 40, the sorbitan monooleate sold by Croda under the name Span 80 V or the sorbitan trioleate sold by Uniqema under the name Span 85 V. Preferably, the sorbitan ester used is sorbitan tristearate.

The ester of $C_{16}$-$C_{22}$ fatty acid and of sorbitan may be present in the composition according to the invention in a content ranging for example from 0.01% to 10% by weight, with respect to the total weight of the composition, preferably ranging from 0.01% to 5% by weight and preferentially ranging from 0.1% to 3% by weight.

The ester of glycerol and of fatty acid can be obtained in particular from an acid comprising a saturated linear alkyl chain having from 16 to 22 carbon atoms. Mention may in particular be made, as ester of glycerol and of fatty acid, of glyceryl stearate (glyceryl mono-, di- and/or tristearate) (CTFA name: Glyceryl stearate), glyceryl ricinoleate and their mixtures. Preferably, the ester of glycerol and of fatty acid used is chosen from glyceryl stearates.

The ester of glycerol and of fatty acid can be present in an amount ranging for example from 0.1% to 10% by weight, with respect to the total weight of the composition, preferably ranging from 0.1% to 5% by weight and preferentially ranging from 0.1% to 3% by weight.

The composition of the invention can comprise in particular a mixture of glyceryl stearate and of polyethylene glycol 100 EO monostearate and in particular that comprising such a mixture in proportions by weight of 50/50 sold under the name Arlacel 165 by Croda.

The composition according to the invention comprises a polycondensate of ethylene oxide and of propylene oxide and more particularly a copolymer consisting of polyethylene glycol and polypropylene glycol blocks, such as, for example, polyethylene glycol/polypropylene glycol/polyethylene glycol triblock polycondensates. These triblock polycondensates have, for example, the following chemical structure:

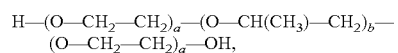

in which formula a ranges from 2 to 150 and b ranges from 1 to 100; preferably, a ranges from 10 to 130 and b ranges from 20 to 80.

The polycondensate of ethylene oxide and of propylene oxide preferably has a weight-average molecular weight ranging from 1000 to 15 000, better still ranging from 1500 to 15 000, in particular ranging from 1500 to 10 000 and even better still ranging from 1500 to 5000.

Advantageously, the said polycondensate of ethylene oxide and of propylene oxide has a cloud temperature, at 10 g/l in distilled water, of greater than or equal to 20° C., preferably of greater than or equal to 60° C. The cloud temperature is measured according to Standard ISO 1065.

Mention may be made, as polycondensate of ethylene oxide and of propylene oxide which can be used according to the invention, of the polyethylene glycol/polypropylene glycol/polyethylene glycol triblock polycondensates sold under the "Synperonic" names, such as "Synperonic® PE/F32" (INCI name: Poloxamer 108), "Synperonic® PE/F108" (INCI name: Poloxamer 338), "Synperonic® PE/L44" (INCI name: Poloxamer 124), "Synperonic® PE/L42" (INCI name: Poloxamer 122), "Synperonic® PE/F127" (INCI name: Poloxamer 407), "Synperonic® PE/F88" (INCI name: Poloxamer 238) or "Synperonic® PE/L64" (INCI name: Poloxamer 184), by Croda or also "Lutrol® F68" (INCI name: Poloxamer 188), sold by BASF.

The polycondensate of ethylene oxide and of propylene oxide can be present in the composition according to the invention in a content ranging for example from 0.01% to 5% by weight, with respect to the total weight of the composition, preferably ranging from 0.05% to 3% by weight and preferentially ranging from 0.05% to 1% by weight.

The composition according to the invention can comprise a fatty alcohol having from 12 to 22 carbon atoms, in particular having from 14 to 18 carbon atoms. Such a fatty alcohol can be chosen, for example, from lauryl alcohol, cetyl alcohol or stearyl alcohol. This fatty alcohol can be present in the composition according to the invention in a content ranging for example from 0.05% to 10% by weight, with respect to the total weight of the composition, preferably ranging from 0.1% to 5% by weight and preferentially ranging from 1% to 5% by weight.

The composition can also comprise a fatty acid having from 12 to 22 carbon atoms, in particular from 14 to 18 carbon atoms. Such a fatty acid can be chosen from lauric acid, myristic acid, cetylic acid (or palmitic acid), stearic acid or cetearic acid.

This fatty acid can be present in the composition according to the invention in a content ranging for example from 0.05% to 10% by weight, with respect to the total weight of the composition, preferably ranging from 0.1% to 5% by weight and preferentially ranging from 1% to 5% by weight.

The composition according to the invention can additionally comprise an anionic surfactant chosen from alkali metal cetyl phosphate salts. The alkali metal salts are, for example, the sodium salts or the potassium salts. The ionic surfactant is preferably potassium cetyl phosphate.

Use may in particular be made of the monopotassium monocetyl phosphate salt (INCI name: potassium cetyl phosphate) sold under the name "Amphisol K" by DSM Nutritional Products.

This anionic surfactant makes it possible to improve the stability of the composition at high temperature (45° C.) for 2 months.

The anionic surfactant can be present in the composition according to the invention in a content ranging for example from 0.05% to 5% by weight, with respect to the total weight of the composition, preferably ranging from 0.5% to 3% by weight and preferentially ranging from 0.1% to 3% by weight.

The composition according to the invention can comprise a hydrophilic gelling agent which makes it possible to thicken the aqueous phase of the composition.

The hydrophilic gelling agent can be chosen, for example, from:

(i) carboxyvinyl polymers (such as optionally crosslinked acrylic acid polymers), such as the products sold under the Carbopol names (INCI name: Carbomer) by Goodrich;

(ii) polyacrylamides and polymers and copolymers of 2-acrylamido-2-methylpropanesulphonic acid which are optionally crosslinked and/or neutralized, such as the poly(2-acrylamido-2-methylpropanesulphonic acid) sold by Hoechst under the name "Hostacerin AMPS" (INCI name: ammonium polyacryloyldimethyltauratic); crosslinked anionic copolymers of acrylamide and of AMPS which are provided in the form of an emulsion, such as those sold under the name of Sepigel 305 (CTFA name: Polyacryl-amide/$C_{13-14}$ Isoparaffin/Laureth-7) and under the name of Simulgel 600 (CTFA name: Acrylamide/Sodium acryloyldimethyltaurate copolymer/Isohexadecane/Polysorbate 80) by SEPPIC; crosslinked anionic copolymers of acrylic acid and of AMPS which are provided in the form of an emulsion, such as those sold under the name of Simulgel EG (CTFA name: Sodium acrylate/Sodium acryloyldimethyltaurate copolymer/Isohexadecane/Polysorbate 80); 2-acrylamido-2-methylpropanesulphonic acid/ethoxylated $C_{12}$-$C_{14}$ alkyl methacrylate copolymers (Aristoflex LNC from Clariant) or 2-acrylamido-2-methylpropanesulphonic acid/ethoxylated stearyl methacrylate copolymers (Aristoflex HMS and Aristoflex SNC from Clariant);

(iii) polysaccharides, such as xanthan gums, guar gums, alginates or cellulose polymers, such as hydroxyethyl cellulose, hydroxypropyl cellulose or carboxymethyl cellulose;

(iv) inorganic compounds, such as smectites or hectorites which may or may not be modified, such as the Bentone products sold by Rheox, the Laponite products sold by Southern Clay Products or the Veegum HS product sold by R.T. Vanderbilt; and their mixtures.

The choice will more particularly be made, among these hydrophilic gelling agents, of the polysaccharides described above, in particular xanthan gum.

The hydrophilic gelling agent can be present in the composition according to the invention in a content ranging for example from 0.01% to 10% by weight, with respect to the total weight of the composition, preferably ranging from 0.1% to 5% by weight and preferentially ranging from 0.1% to 3% by weight.

The composition according to the invention comprises an aqueous phase.

The composition can comprise water in a content ranging for example from 20% to 95% by weight, with respect to the total weight of the composition, preferably ranging from 30% to 90% by weight and preferentially ranging from 40% to 70% by weight.

The water can be a floral water, such as cornflower water, and/or a mineral water, such as water from Vittel, water from Lucas or water from La Roche-Posay, and/or a thermal water.

The composition can additionally comprise an organic solvent which is miscible with water at ambient temperature (25° C.) and which is chosen in particular from monoalcohols having from 2 to 6 carbon atoms, such as ethanol or isopropanol;

polyols having in particular from 2 to 20 carbon atoms, preferably having from 2 to 10 carbon atoms and preferentially having from 2 to 6 carbon atoms, such as glycerol, propylene glycol, butylene glycol, pentylene glycol, hexylene glycol, dipropylene glycol or diethylene glycol;

glycol ethers (having in particular from 3 to 16 carbon atoms), such as mono-, di- or tripropylene glycol ($C_1$-$C_4$) alkyl ethers or mono-, di- or triethylene glycol ($C_1$-$C_4$) alkyl ethers;

and their mixtures.

Advantageously, the aqueous phase can comprise ethanol.

The composition according to the invention can comprise an organic solvent which is miscible with water at ambient temperature, in particular a polyol, in a content ranging for example from 1% to 20% by weight, with respect to the total weight of the composition, preferably ranging from 3% to 15% by weight.

Advantageously, the composition according to the invention has a pH ranging for example from 3.0 to 8.0, preferably ranging from 3.5 to 7.0, preferentially ranging from 3.5 to 6.0 and more preferentially ranging from 3.5 to 5.5.

The emulsion according to the invention also comprises an oily phase.

Mention may be made, as oils which can more particularly be used in the composition of the invention, for example, of:
  hydrocarbon oils of animal origin, such as perhydrosqualene (or squalane);
  synthetic esters and ethers, in particular of fatty acids, such as oils of formulae $R^1COOR^2$ and $R^1OR^2$ in which $R^1$ represents the residue of a fatty acid comprising from 8 to 29 carbon atoms and $R^2$ represents a linear or branched hydrocarbon chain comprising from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate and diethylene glycol diisononanoate; pentaerythritol esters, such as pentaerythrityl tetraisostearate; or lipophilic derivatives of amino acids, such as Isopropyl lauroyl sarcosinate (INCI name), sold under the name Eldew SL 205 by Ajinomoto;
  linear or branched hydrocarbons of mineral or synthetic origin, such as mineral oils (mixture of hydrocarbon oils derived from oil; INCI name: Mineral oil), volatile or nonvolatile liquid paraffins and their derivatives, liquid petrolatum, polydecenes, isohexadecane, isododecane or hydrogenated isoparaffin, such as Parleam® oil, sold by NOF Corporation (INCI name: Hydrogenated polyisobutene);
  silicone oils, such as volatile or nonvolatile poly-methylsiloxanes (PDMS) comprising a linear or cyclic silicone chain which are liquid or pasty at ambient temperature, in particular cyclopolydimethylsiloxanes (cyclomethicones), such as cyclopentasiloxane and cyclohexadimethylsiloxane; polydimethylsiloxanes comprising pendant alkyl, alkoxy or phenyl groups or alkyl, alkoxy or phenyl groups at the end of the silicone chain, which groups have from 2 to 24 carbon atoms; or phenylated silicones, such as phenyl trimethicones, phenyl dimethicones, phenyl(trimethylsiloxy)diphenylsiloxanes, diphenyl dimethicones, diphenyl(methyldiphenyl)trisiloxanes, (2-phenylethyl)trimethylsiloxysilicates and polymethylphenylsiloxanes;
  fluorinated oils, such as those which partially comprise hydrocarbon and/or silicone, such as those described in the document JP-A-2-295912;
  ethers, such as Dicaprylyl ether (CTFA name); and benzoates of $C_{12}$-$C_{15}$ fatty alcohols (Finsolv TN from Finetex);
  their mixtures.

The oil can be present in the composition according to the invention in a content ranging for example from 1% to 50% by weight, with respect to the total weight of the composition, preferably ranging from 5% to 40% by weight and preferentially ranging from 5% to 30% by weight.

The oily phase of the emulsion can comprise other fatty substances, such as waxes; gums, such as silicone gums (dimethiconol); silicone resins, and their mixtures.

The composition according to the invention can comprise at least one organic photoprotective agent which is active in the UV-A and/or UV-B regions (absorbers) and which is soluble in water or fatty substances or else insoluble in the cosmetic solvents commonly used.

As the composition according to the invention exhibits good stability, it is suitable for the formulation of organic UV screening agents: the UV screening agents incorporated in the composition are not decomposed in the presence of ascorbic acid compound.

The organic screening agents are chosen in particular from anthranilates; cinnamic derivatives; dibenzoyl-methane derivatives; ascorbic derivatives; camphor derivatives, triazine derivatives, such as those described in Patent Applications U.S. Pat. No. 4,367,390, EP 863 145, EP 517 104, EP 570 838, EP 796 851, EP 775 698, EP 878 469, EP 933 376, EP 507 691, EP 507 692, EP 790 243 and EP 944 624; benzophenone derivatives; β,β-diphenylacrylate derivatives; benzotriazole derivatives; benzalmalonate derivatives; benz-imidazole derivatives; imidazolines; bis-benzoxazolyl derivatives, such as described in Patents EP 669 323 and U.S. Pat. No. 2,463,264; p-aminobenzoic acid (PABA) derivatives; methylenebis(hydroxyphenylbenzotriazole) derivatives, such as described in Applications U.S. Pat. No. 5,237,071, U.S. Pat. No. 5,166,355, GB 2 303 549, DE 197 26 184 and EP 893 119; screening polymers and screening silicones, such as those described in particular in Application WO 93/04665; dimers derived from α-alkylstyrene, such as those described in Patent Application DE 19 855 649; 4,4-diarylbutadienes, such as described in Applications EP 0 967 200, DE 19 746 654, DE 19 755 649, EP-A-1 008 586, EP 1 133 980 and EP 133 981, and their mixtures.

Advantageously, use is made of a nonionic organic protective screening agent.

The photoprotective agent can be present in the composition according to the invention in a content ranging for example from 0.01% to 30% by weight, with respect to the total weight of the composition, preferably ranging from 0.1% to 25% by weight and preferentially ranging from 0.1% to 20% by weight.

The composition according to the invention can additionally comprise fillers.

The term "fillers" should be understood as meaning colourless or white and inorganic or organic particles of any shape which are insoluble in the medium of the composition, whatever the temperature at which the composition is manufactured, and which do not colour the composition.

The fillers can be of any shape, platelet, spherical or oblong, whatever the crystallographic form (for example, sheet, cubic, hexagonal, orthorhombic, and the like). Mention may be made of: talc, mica, silica, kaolin, powders formed of poly-β-alanine and polyethylene, powders formed of tetrafluoroethylene polymers (Teflon®), lauroyllysine, starch, boron nitride, hollow polymeric microspheres, such as those of poly(vinylidene chloride)/acrylonitrile, such as Expancel® (Nobel Industrie), or of acrylic acid copolymers, silicone resin microbeads (Tospearls® from Toshiba, for example), polyorganosiloxane elastomer particles, precipitated calcium carbonate, magnesium carbonate, basic magnesium carbonate, hydroxyapatite, barium sulphate, aluminium oxides, polyurethane powders, composite fillers, hollow silica microspheres and glass or ceramic microcapsules.

The fillers can be present in the composition in a content ranging for example from 0.1% to 15% by weight, preferably ranging from 0.1% to 10% by weight and preferentially ranging from 0.1% to 5% by weight, with respect to the total weight of the composition.

The composition according to the invention can additionally comprise an active agent chosen from desquamating agents, capable of acting either by promoting exfoliation or on the enzymes involved in the desquamation or decomposition of the corneodesmosomes, moisturizing agents, depigmenting or propigmenting agents, antiglycation agents, NO-synthase inhibitors, 5α-reductase inhibitors, lysyl and/or prolyl hydroxylase inhibitors, agents which stimulate the synthesis of dermal or epidermal macromolecules and/or which prevent their decomposition, agents which stimulate the proliferation of fibroblasts or keratinocytes and/or the differentiation of keratinocytes, muscle relaxants, antimicrobial agents, tightening agents, agents for combating pollution or free radicals, anti-inflammatories, lipolytic active principles or active principles having a favourable activity, direct or indirect, on the reduction in adipose tissue, agents which act on the microcirculation and agents which act on the energy metabolism of the cells.

The composition according to the invention is intended in particular for a topical use, in particular a cosmetic or dermatological topical use.

In a known way, the cosmetic or dermatological composition of the invention can also comprise adjuvants usual in the cosmetic or dermatological field, such as preservatives, fragrances, bactericides, odour absorbers, colouring materials, salts, surfactants, thickeners or bases. The amounts of these various adjuvants are those conventionally used in the field under consideration, for example from 0.01 to 20% of the total weight of the composition. These adjuvants, depending on their nature, can be introduced into the fatty phase or into the aqueous phase.

The composition according to the invention can be applied to the skin or lips, according to the use for which it is intended. It can thus be used in a method for the cosmetic treatment of the skin comprising the application of the composition according to the invention to the skin, for example for the purpose of toning it up, of regenerating it or of smoothing out its wrinkles and/or for combating ageing of the skin or the damaging effects of UV radiation and/or for strengthening skin tissues against attacks from the surroundings.

In an alternative form, the composition according to the invention can be used for the manufacture of a dermatological preparation.

The composition can be a care composition, in particular can be a product for caring for the skin, such as a care base for the skin, a care cream (day cream, night cream, antiwrinkle cream) or a makeup base; a care composition for the lips (lip balm); or a sun-protection or self-tanning composition.

The composition can also be a makeup composition, in particular a composition for making up the skin or lips. In particular, the makeup composition can be a foundation, a blusher, an eyeshadow, a concealer or a product for making up the body.

Advantageously, the composition is a leave-in composition.

The emulsion according to the invention can be prepared according to the following general procedure: The constituents of the aqueous phase are mixed by heating at a temperature of approximately 70° C. The oils, the active principle of formula (I) and the surfactants are furthermore mixed by heating at a temperature of approximately 80° C. The fatty phase is run into the aqueous phase at a temperature of approximately 70° C. and then the mixture is stirred for 10 minutes at high speed using a turbine mixer. The emulsion obtained is cooled to approximately 60° C. The thickeners are subsequently added and then the mixture is again stirred for 10 minutes. The other active principles are subsequently optionally introduced.

The invention will now be illustrated using the following nonlimiting examples.

EXAMPLE 1 AND COMPARATIVE EXAMPLE 1b

A composition for caring for the face in the form of an oil-in-water emulsion according to the invention was prepared (Example 1) which has the following composition:

| | |
|---|---|
| Mixture of glyceryl monostearate and of polyethylene glycol (100 EO) stearate (Arlacel 165 FL from Croda) | 1.6 g |
| Oxyethyleneated (20 EO) sorbitan monostearate (Tween 60 from Croda) | 0.7 g |
| Cetyl alcohol | 1 g |
| Stearic acid | 0.5 g |
| Apricot kernel oil | 5 g |
| Polydimethylsiloxane 10 cSt | 7.0 g |
| Hydrogenated isoparaffin (Parleam from NOF Corporation) | 2.0 g |
| 4-(1-Phenylethyl)-1,3-dihydroxybenzene | 0.3 g |
| Polyacrylamidomethylpropanesulphonic acid partially neutralized with ammonia and highly crosslinked (Hostacerin AMPS from Clariant) | 1.0 g |
| Xanthan gum | 0.3 g |
| Silica microspheres (SB700 from Myoshi Kasei) | 3.0 g |
| EO-PO-EO (128 EO/54 PO/128 EO) block copolymer (Synperonic ® PE/F108 from Croda) | 0.4 g |
| Glycerol | 5 g |
| Disodium salt of ethylenediaminetetraacetic acid | 0.2 g |
| Preservatives | q.s. |
| Water | q.s. for 100 g |

A similar composition to Composition 1 but additionally comprising 1.5 g of potassium cetyl phosphate (Composition 1a according to the invention) was also prepared (amount added by deleting the same weight of water).

A similar composition to Composition 1 but not comprising EO-PO-EO block copolymer (Synperonic® PE/F108 from Croda) (Composition 1b, not forming part of the invention) was also prepared (amounts deleted replaced by the same weight of water).

The emulsions of Examples 1 and 1a have good stability after 24 hours at 55° C. and also after 2 months at 45° C. When observed under a microscope, the emulsion obtained is fine and dense.

The composition is applied to the face for daily use during the day.

The comparative emulsion of Example 1b is unstable after 24 hours at 55° C. and after storing for 2 months at 45° C.: the emulsion, observed under a microscope, is coarser and more degraded. Phase separation is observed with the naked eye, with release at the surface of the oily phase.

EXAMPLE 2, 2a AND COMPARATIVE EXAMPLE 2b

A composition for caring for the face in the form of an oil-in-water emulsion was prepared which has the following composition (Example 2):

| | |
|---|---|
| Mixture of glyceryl monostearate and of polyethylene glycol (100 EO) stearate (Arlacel 165 FL from Croda) | 0.5 g |
| Stearic acid | 1 g |
| Cetyl alcohol | 0.5 g |
| Isocetyl stearate | 5 g |
| 4-(1-Phenylethyl)-1,3-dihydroxybenzene | 0.5 g |
| Drometrizole trisiloxane (Silitrizole from Rhodia) | 1 g |
| Caprylic/capric (60/40) acid triglycerides | 3 g |
| 5-(n-Octanoyl) salicylic acid | 0.3 g |
| Tocopheryl acetate | 1 g |
| Ascorbyl glucoside | 0.05 g |
| Xanthan gum (Rhodicare XC from Rhodia) | 0.15 g |
| Acrylamide/sodium 2-acrylamido-2-methylpropanesulphonate copolymer as an inverse emulsion at 40% in isoparaffin/water (Sepigel 305 from Seppic) | 1.8 g |
| Sodium hexametaphosphate | 0.05 g |
| Disodium salt of ethylenediaminetetraacetic acid | 0.05 g |
| EO-PO-EO block copolymer (Synperonic ® PE/F108 from Croda) | 0.4 g |
| Glycerol | 7 g |
| Butylene glycol | 3 g |
| Preservatives | q.s. |
| Fragrance | q.s. |
| Water | q.s. for 100 g |

A similar composition to Example 2 but additionally comprising 1.5 g of potassium cetyl phosphate (Composition 2a) was also prepared (amount added by deleting the same weight of water).

A similar composition to Example 2 but not comprising EO-PO-EO block copolymer (Synperonic® PE/F108 from Croda) and potassium cetyl phosphate (Composition 2b, not forming part of the invention) was also prepared (amounts deleted replaced by the same weight of water).

The emulsions of Examples 2 and 2a have good stability after 24 hours at 55° C. When observed under a microscope, the emulsion obtained is fine and dense. The emulsion 2a additionally has good stability after 2 months at 45° C.

The composition is applied to the face for daily use during the day.

The comparative emulsion of Example 2b is unstable after storing for 2 months at 45° C.: the emulsion, observed under a microscope, is coarser and more degraded. Phase separation with release at the surface of the oily phase is observed with the naked eye.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition in the form of an oil-in-water emulsion, comprising oil, water, and:

from 0.1 to 10% by weight, based on the total weight of the composition, of an ester of fatty acid and of polyethylene glycol;

from 0.1 to 10% by weight, based on the total weight of the composition, of a surfactant chosen from esters of $C_{16}$-$C_{22}$ fatty acid and of sorbitan and esters of $C_{16}$-$C_{22}$ fatty acid and of glycerol;

from 0.01 to 5% by weight, based on the total weight of the composition, of a polyethylene glycol/polypropylene glycol/polyethylene glycol triblock polycondensate having the following chemical structure:

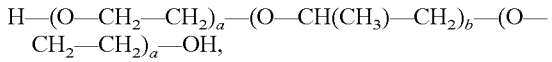

in which formula a ranges from 2 to 150 and b ranges from 1 to 100, and having a weight-average molecular weight of 1,000 to 15,000;

from 0.01 to 5% by weight, based on the total weight of the composition, of a hydroxylated diphenylmethane derivative of formula (I):

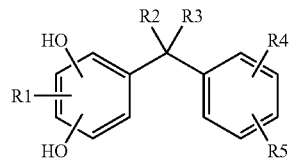

in which:

R1 is chosen from a hydrogen atom, a methyl group, a saturated or unsaturated and linear or branched alkyl chain having from 2 to 4 carbon atoms, an OH group and a halogen, R2 is chosen from a hydrogen atom, a methyl group or a saturated or unsaturated and linear or branched alkyl chain having from 2 to 5 carbon atoms, R3 is chosen from a methyl group or a saturated or unsaturated and linear or branched alkyl chain having from 2 to 5 carbon atoms, R4 and R5 are chosen, independently of one another, from a hydrogen atom, a methyl group, a saturated or unsaturated and linear or branched alkyl chain having from 2 to 5 carbon atoms, an —OH group or a halogen.

2. The composition according to claim 1, wherein the hydroxylated diphenylmethane derivative has the following formula (II):

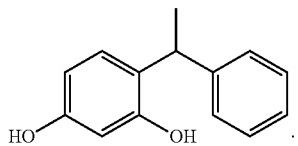

3. The composition according to claim 1, wherein the ester of fatty acid and of polyethylene glycol is chosen from $C_{16}$-$C_{22}$ fatty acid esters comprising from 8 to 100 ethylene oxide units.

4. The composition according to claim 1, wherein the ester of fatty acid and of polyethylene glycol is chosen from polyethylene glycol stearates.

5. The composition according to claim 1, wherein the ester of fatty acid and of polyethylene glycol comprises from 20 to 40 ethylene oxide units.

6. The composition according to claim 1, wherein it comprises an ester of $C_{16}$-$C_{22}$ fatty acid and of sorbitan chosen from sorbitan stearates.

7. The composition according to claim 1, wherein it comprises an ester of $C_{16}$-$C_{22}$ fatty acid and of glycerol chosen from glyceryl stearates.

8. The composition according to claim 1, wherein it comprises a mixture of glyceryl stearate and of polyethylene glycol 100 EO monostearate.

9. The composition according to claim 1, further comprising a hydrophilic gelling agent.

10. The composition according to claim 9, wherein the hydrophilic gelling agent is a polysaccharide.

11. The composition according to claim 1, further comprising a cosmetic or dermatological adjuvant chosen from UV screening agents, fillers, preservatives, fragrances, bactericides, odour absorbers, colouring materials, salts, surfactants, thickeners and bases.

12. The composition according to claim 1, wherein the ester of fatty acid and of polyethylene glycol is chosen from polyethylene glycol stearates comprising from 20 to 40 ethylene oxide units, and wherein the ester of $C_{16}$-$C_{22}$ fatty acid and of sorbitan is chosen from sorbitan stearates and the ester of $C_{16}$-$C_{22}$ fatty acid and of glycerol is chosen from glyceryl stearates.

13. The composition according to claim 1, wherein the composition comprises glyceryl stearate, polyethylene glycol 100 EO monostearate, and a polyethylene glycol/polypropylene glycol/polyethylene glycol triblock polycondensate.

14. The composition according to claim 2, wherein the composition comprises glyceryl stearate, polyethylene glycol 100 EO monostearate, and a polyethylene glycol/polypropylene glycol/polyethylene glycol triblock polycondensate.

15. The composition according to claim 1, which shows no phase separation observable by the naked eye after storage for 24 hours at 55° C.

16. The composition according to claim 1, which shows no phase separation observable by the naked eye after storage for 2 months at 45° C.

17. The composition according to claim 1, comprising from 5 to 30 wt % of oil, based on the total weight of the composition.

18. The composition according to claim 1, wherein the polycondensates is contained in an amount of from 0.05 to 3% by weight, with respect to the total weight of the composition.

19. A method for caring for or making up a keratinous substance, comprising applying the composition of claim 1 to a keratinous substance.

* * * * *